(12) United States Patent
Yamamori et al.

(10) Patent No.: US 6,258,040 B1
(45) Date of Patent: Jul. 10, 2001

(54) AIRWAY ADAPTER FOR NON-DISPERSIVE INFRARED GAS ANALYZER

(75) Inventors: Shinji Yamamori; Noriaki Todokoro; Hidetoshi Dainobu, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/397,118

(22) Filed: Sep. 16, 1999

(30) Foreign Application Priority Data

Sep. 16, 1998 (JP) .................................................. 10-261066

(51) Int. Cl.[7] .............................. A61B 5/08; G01N 1/22; G01N 21/00; G01N 31/00; G01J 5/02
(52) U.S. Cl. ......................... 600/529; 600/532; 73/23.3; 73/23.37; 250/343; 250/339.13; 356/437
(58) Field of Search ....................................... 600/529, 532, 600/538; 73/23.2, 23.3, 23.37; 250/343, 339.13; 356/437; 422/84

(56) References Cited

U.S. PATENT DOCUMENTS

| | | | |
|---|---|---|---|
| 5,067,492 | * | 11/1991 | Yelderman et al. .................. 600/532 |
| 5,095,900 | * | 3/1992 | Fertig et al. ........................... 600/532 |
| 6,044,843 | * | 4/2000 | O'Neil et al. ......................... 600/529 |
| 6,095,986 | * | 8/2000 | Braig et al. ........................... 600/532 |

* cited by examiner

*Primary Examiner*—Eric F. Winakur
*Assistant Examiner*—Navin Natnithithadha
(74) *Attorney, Agent, or Firm*—Sughrue, Mion, Zinn, Macpeak & Seas, PLLC

(57) ABSTRACT

A transparent sheet 11 for transmitting an infrared ray therethrough is formed by laminating a PET sheet 5 on which a anti-fogging layer 4 can be formed easily and a PP sheet 12 with good infrared ray transmission property, thereby to make the thickness of the transparent window larger.

4 Claims, 6 Drawing Sheets

→ EXPIRED AIR

AIRWAY ADAPTER FOR NON-DISPERSIVE INFRARED GAS ANALYZER

BACKGROUND OF INVENTION

1. Field of Invention

The present invention relates to an airway adapter for a non-dispersive infrared gas analyzer in which an infrared ray passes through apertures provided at opposite side wall portions of a flow tube, and an infrared ray detector measures an amount of the infrared ray which is absorbed and attenuated by gas flowing within the flow tube thereby to measure a concentration of the gas. In particular, the present invention relates to an airway adapter for a non-dispersive infrared gas analyzer which is provided between a patient and a respirator or an anesthesia machine and which measures the concentrations of various gases within a respiratory gas.

2. Related Art

When a mechanical ventilator assists a patient in breathing, an airway adapter is attached to a flow path between the patient and a mechanical ventilator and a concentration of carbon dioxide within the respiratory gas is measured. FIG. 12 is a perspective view showing an example of the outward appearance of a generally known airway adapter. In FIG. 12, the center portion of a cylindrical flow tube 1 along the axial direction thereof is formed in a rectangular tubular shape in section. Circular aperture portions 2 formed by openings for passing an infrared ray therethrough are provided at opposite positions of both side walls of the flow tube, respectively. Transparent windows 3 formed by transparent films configured in a circular plate shape are hermetically attached to the aperture portions 2, respectively.

As the transparent window 3, there has been employed sapphire or a plastic sheet formed by a single sheet on which an anti-fogging layer is formed. As the plastic sheet, there has been employed a polyester sheet (hereinafter called a PET sheet) 5 on which a anti-fogging layer 4 can be easily formed by coating or deposition, as shown in FIG. 13.

However, when the sapphire is employed as the material of the transparent window 3, there arises a problem that the cost of the transparent window is expensive. Further, in this case, disadvantageously it is required to heat the transparent window by using a heater to prevent a condensation of water in the respiratory gas on the surface of the sapphire.

The PET sheet 5 on which the anti-fogging layer 4 is formed may be used as the transparent window 3 in place of the expansive sapphire. In this case, the cost for manufacturing the airway adapter can be reduced. Further, since the anti-fogging layer is hydrophilic, a thin water layer instead of water drops is formed on the surface of the transparent window 3, whereby an infrared ray transmits through the transparent windows 3 without being scattered and so the transparent windows do not fog. Thus, the PET sheet has such an advantage that, since it is not necessary to heat the PET sheet by using a heater, the configuration of the analyzer can be simplified and the power consumption of the analyzer can be reduced. However, the PET sheet 5 is required to be made thinner in order to improve the transmittance of the infrared ray since it absorbs infrared rays. If the PET sheet is made thinner, the PET sheet is likely damaged by the heat or mechanical impact. Further, if the PET sheet 5 is made thinner, there arises a problem that, in the case where a water layer is formed on the surface of the anti-fogging layer 4, the measured value of the gas concentration may contain an error due to the optical interference.

Polypropylene and polyethylene materials have good transmittance for an infrared ray. The transparent window 3 can be made sufficiently thick by using such material. However, in this case, the anti-fogging layer 4 can not be formed on the surface of the transparent window since each of the polypropylene and polyethylene is not good in adhesive property.

SUMMARY OF INVENTION

The present invention has been performed in view of the aforesaid conventional problems.

An object of the present invention is to provide an airway adapter for a non-dispersive infrared gas analyzer having transparent windows on anti-fogging layers which have good heat-resistance properties, mechanical strength and good transmittance and hardly causes optical interference.

In order to achieve the aforesaid object, according to the present invention, there is arranged in an airway adapter for a non-dispersion infrared ray gas analyzer including a flow tube for passing gas therethrough, aperture portions respectively formed by openings provided at opposite positions of a side wall of the flow tube which transmit an infrared ray therethrough, and transparent films hermetically attached to the aperture portions respectively, wherein each of the transparent films is formed by a plurality of layers including a first film which is capable of forming the anti-fogging layer on a surface thereof and a second film for transmitting the infrared ray therethrough with a good transmittance, each of the films for a anti-fogging layer is disposed at an inner side of the flow tube, and each of the anti-fogging layers is formed on the surface of the first film.

The present invention provides an airway adapter which has the films for a anti-fogging layer formed by a polyester sheet and the good transmittance films formed by a polypropylene sheet. The present invention provides an airway adapter which has the films for an anti-fogging layer formed by a polyester sheet and the good transmittance films formed by a polypropylene sheet.

According to the aforesaid configuration of the present invention, since the polypropylene sheet (hereinafter called a PP sheet) with good transmittance and a PET sheet are laminated, the transparent film can be made thicker without reducing an amount of infrared ray which transmits therethrough. As a result, the transparent film can be improved in heat-resistance property and mechanical strength. Further, even in the case where a water layer is formed on the anti-fogging layer due to water vapor in a respiratory gas, it can be prevented that the measured value of the gas concentration contains an error due to the optical interference of the light.

DETAIL DESCRIPTION OF PREFERRED EMBODIMENTS

DETAILED DESCRIPTION OF PREFERRED EMBODIMENTS

Figure 1:
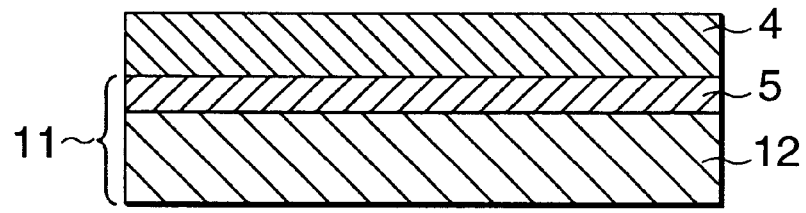
FIG. 1 is a sectional view showing an example of the arrangement of the transparent film used in an airway adapter for a non-dispersive infrared gas analyzer according to an embodiment of the present invention.
Figure 12:
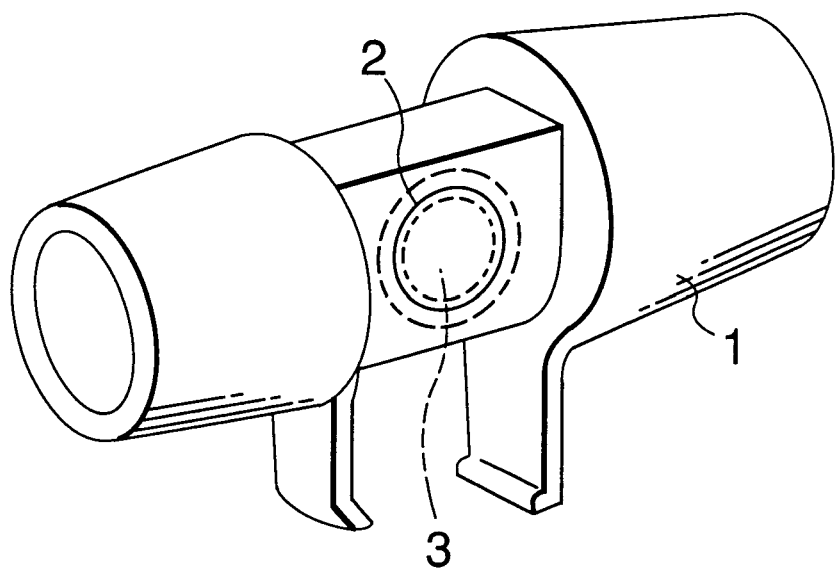
FIG. 12 is a perspective view showing an example of the outward appearance of a generally known airway adapter.
Figure 13:
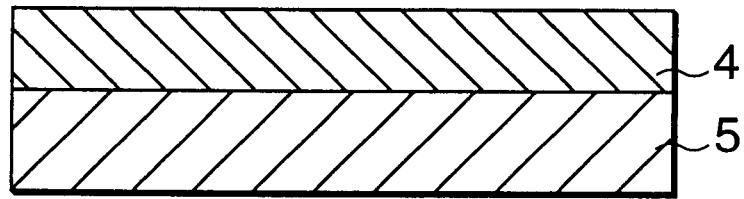
FIG. 13 is a sectional view showing an example of the arrangement of a conventional sheet with anti-fogging layer.

An example of the arrangement of an airway adapter for a non-dispersive infrared gas analyzer according to an embodiment of the present invention will be explained with reference to the accompanying drawings. The entire arrangement of the embodiment is same as the conventional example shown in FIG. 12 and the feature of the present embodiment resides in the arrangement of a transparent film. FIG. 1 is a sectional view showing an example of the arrangement of the transparent film in the present embodiment. In FIG. 1, like parts corresponding to those of the conventional example shown in FIG.13 are marked with the same references and therefor the explanation thereof is omitted suitably.

In FIG. 1, a transparent sheet 11 serving as the transparent film is formed by a PET sheet 5 and a PP sheet 12 which are laminated integrally. In the case where each of the transparent sheets 11 is attached to the corresponding one of aperture portions 2 of a flow tube 1 as shown in FIG. 12, the PET sheets 5 are disposed at the inside of the flow tube. An anti-fogging layer 4 is formed by coating or deposition on the surface of each of the PET sheets 5. A not-shown PP mold ring is thermally fused on the PP sheet 12 of each of the transparent sheets 11, and the ring is fused by means of ultrasonic wave or the like on the inner periphery of each of the aperture portions 2 of the flow tube 1. This eliminates adhesives which require careful handling, dispensing, curing. In order to increase the mechanical strength of the flow tube 1, the tube is formed by PP (polypropylene) in which glass fibers are contained, for example. In this embodiment, the thickness of the anti-fogging layer 4, the PET sheet 5 and the PP sheet 12 are set to be 20$\mu$m, 12$\mu$m and 40$\mu$m, respectively. Of course, the material of the transparent sheets 11 is not limited by this embodiment. Instead of polyester sheet (PET), polycarbonate, vinyl chloride, cellulose acetate of polyimide may be used. In stead of polyester sheet (PET), it is applicable for employing polycarbonate, vinyl chloride, cellulose acetate or polyimide.

Figure 2:
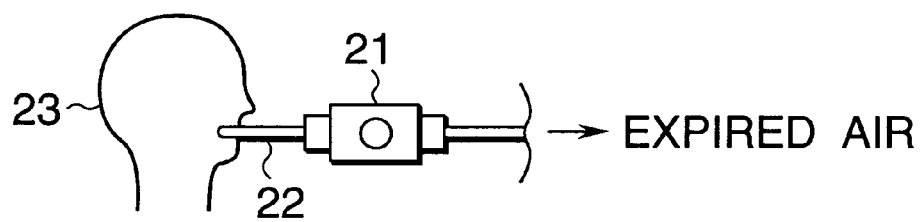
FIG. 2 is an explanatory diagram showing a person in expiration phase using an airway adapter.
Figure 3:
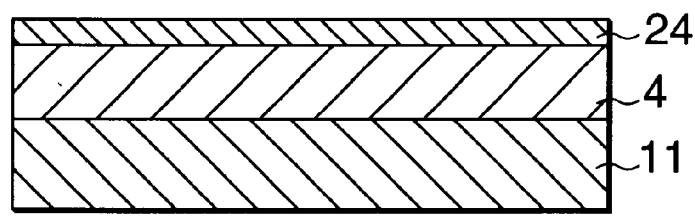
FIG. 3 is a sectional view showing a water layer formed on a anti-fogging layer in expiration phase.

Then, the explanation will be made as to the change of an amount of an infrared ray being transmitted through the anti-fogging layer 4 and the transparent sheet 11, due to the optical interference. As shown in FIG. 2, when a gas being expired from a patient 23 which is humidified in the lungs flows through the airway adapter 21, a water layer 24 is formed on the anti-fogging layer 4 as shown in FIG. 3.

Figure 4:
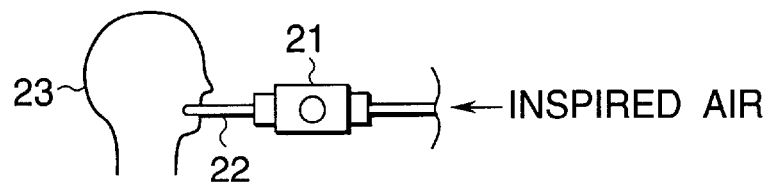
FIG. 4 is an explanatory diagram showing a person in inspiration phase using the airway adapter.
Figure 5:
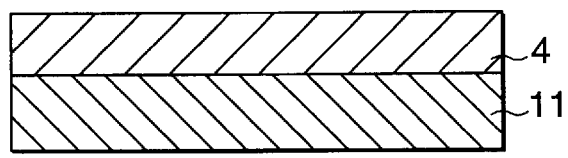
FIG. 5 is a sectional view showing the state on the anti-fogging layer in inspiration phase.

As shown in FIG. 4, when a dry gas being inspired by the patient 23 flows into the airway adapter r21, the water layer 24 on the anti-fogging layer 4 evaporates as shown in FIG. 5. In other words, the thickness of the water layer 24 repeatedly increases and decreases at every expiration and inspiration of the person, and so the entire thickness of the film including the water layer 24 repeatedly increases and decreases.

When the film thickness changes in the aforesaid manner, an amount of the infrared ray being transmitted through the transparent window changes due to the optical interference. Such a phenomenon will be explained hereinafter.

An energy transmittance T of a thin film with a thickness d and a refractive index of n will be given by the following expressions (1) and (2).

$$T=(1-r^2)^2/(1-2r^2 \cos \delta + r^4) \quad (1)$$

$$\delta = 2\pi/\lambda \cdot 2nd \cos \lambda \quad (2)$$

where r represents an amplitude reflectance and $\lambda$ represents a wavelength of light.

Figure 6:
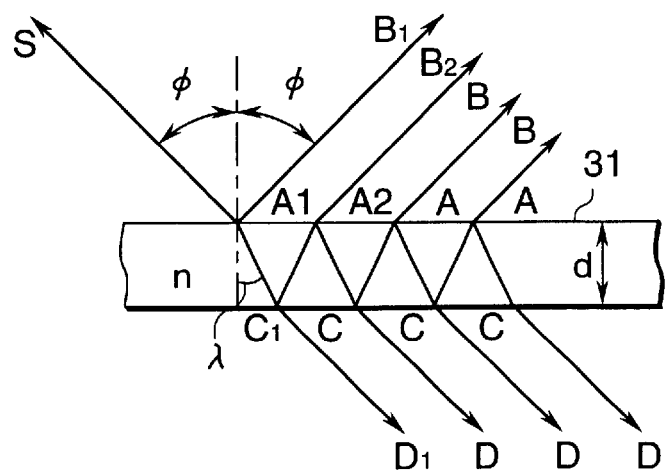
FIG. 6 is an explanatory diagram showing an optical path of a light beam incident on a thin film.

FIG. 6 shows a light path of a light beam emitted from a light source S and incident with an incident angle of $\psi$ on a thin film 31 with a thickness d and a refractive index of n. A part of the incident light beam is reflected at a point Al on the surface of the film as shown by an arrow Bi and the other part of the incident light beam is refracted and incident into the thin film 31. A part of the incident light beam incident into the film is reflected at a point C1 on the rear surface of the thin film 31 and the remaining part thereof is refracted and emitted from the rear surface of the thin film 31 as shown by an arrow D1. A part of the incident light beam reflected at the point C1 is refracted and emitted outward from the surface of the thin film at a point A2 as shown by an arrow Be and remaining part thereof is reflected at the point A2 and transmits within the thin film 31. Hereinafter, the incident light beam is repeatedly refracted and reflected.

Figure 7:
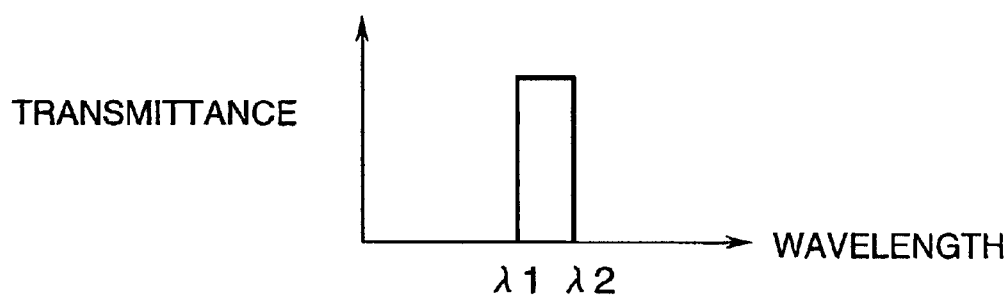
FIG. 7 is a diagram showing the optical characteristics of a band pass filter.
Figure 8:
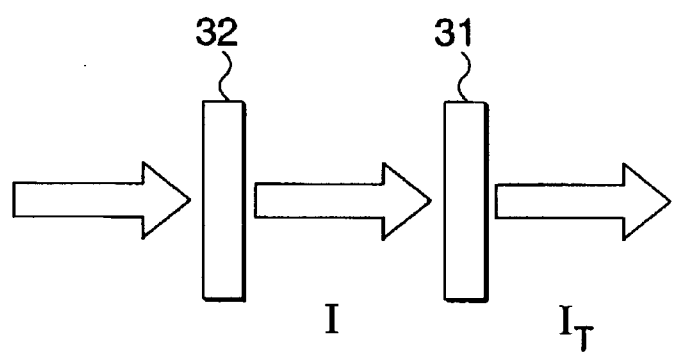
FIG. 8 is an explanatory diagram showing the changes of an intensity of a light beam irradiated from a light source by transmitting through a bandpass filter 32 and thin film 31.
Figure 9:
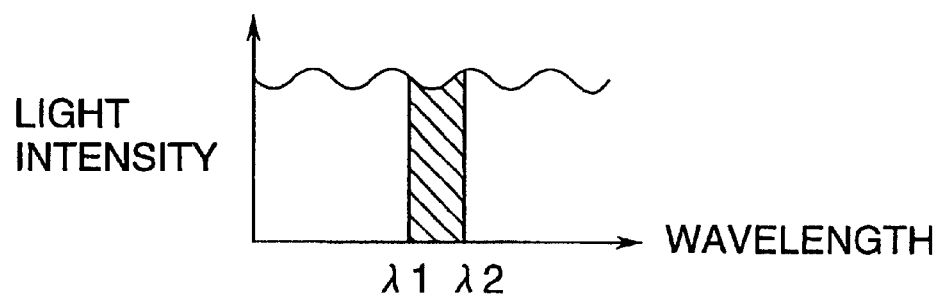
FIG. 9 is a diagram showing an intensity of a light beam transmitting through the bandpass filter.

As clear from the expressions (1) and (2), the transmittance T changes depending on the wavelength $\lambda$ in a manner that the transmittance T repeatedly changes between the maximum and minimum values in accordance with the wavelength $\lambda$ and the repetition period thereof becomes shorter as the thickness d becomes larger. In order to simplify the calculation, supposing that a band-pass filter through which a light beam irradiated from the light source S passes has an optical characteristic shown in FIG. 7, an intensity $I_T$ of the light beam transmitting through the bandpass filter 32 and the thin film 31 in the manner shown in FIG. 8 is proportional to an area of the slanted portion shown in FIG. 9. In this case, it is supposed that an intensity of the light beam incident on the thin film 31 is constant irrespective of the wavelength.

Figure 10:
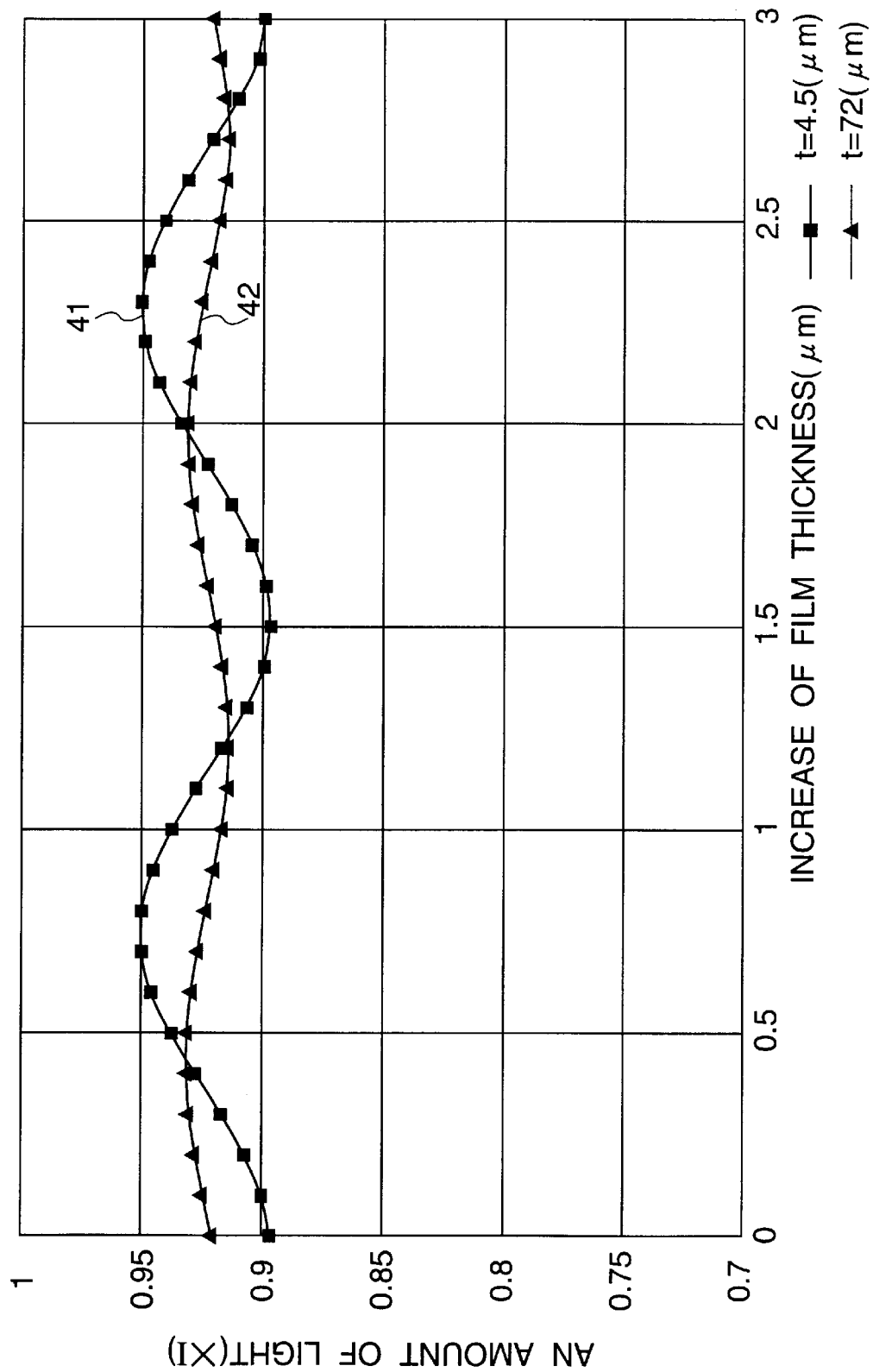
FIG. 10 is a diagram showing the changes of an amount of a light beam when the thickness of a water layer shown in FIG. 3 changes.

When the water layer 24 is formed on the anti-fogging layer 4 as shown in FIG. 3, the entire thickness d of the film increases. The changes of an amount I of the light beam at the time where the thickness of the water layer 24 increases will be shown in FIG. 10 as to the cases where the entire thickness d are 45 $\mu$m and 72 $\mu$m. The filter 32 has such optical characteristics in FIG. 7 that the wavelength $\mu$1 is 4.22 $\mu$m and the wavelength $\mu$2 is 4.32 $\mu$m, and the half-width is 0.1 $\mu$m. A curve 41 represents the case where the thickness d is 45 $\mu$m and a curve 42 represents the case where the thickness d is 72 $\mu$m. As clear from FIG. 10, a changed value of an amount I of the light beam can be made smaller and an error contained in the measured value of the concentration of the carbon dioxide can also be made smaller in the case where the entire thickness of the film is larger.

Figure 11:
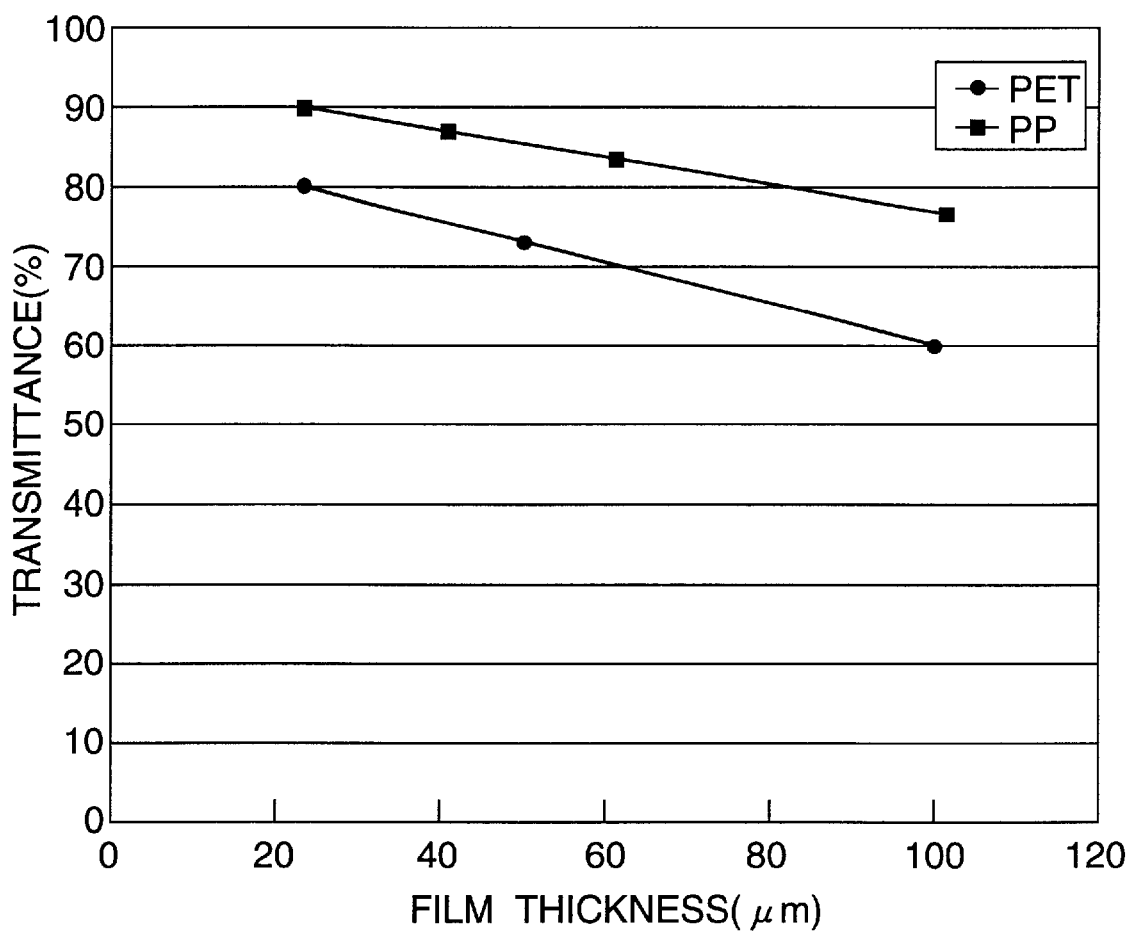
FIG. 11 is a diagram showing the relation between the changes of the thickness of a PET sheet and a PP sheet and a transmittance of an infrared ray.

However, it is not preferable to make the film thickness larger since the PET sheet 5 is not good in the transmission property of the infrared ray. There are polypropylene and polyethylene as the material with good transmission property for the infrared ray. FIG. 11 is a diagram showing the relation between the respective film thickness of the PET sheet and the PP sheet and a transmittance of an infrared ray with a wavelength of 4.3 $\mu$m. As clear from FIG. 11, the transmittance of the PET sheet with a thickness of 25 $\mu$m corresponds to the transmittance of the PP sheet with a thickness of 80 $\mu$m. Accordingly, the film thickness can be made larger without degrading or reducing the transmittance of an infrared ray by employing the PP sheet.

However, since each of polypropylene and polyethylene is chemically stable and does not have a functional group capable of performing covalent bonding nor a group with polarity, the plastic made of such material has drawbacks that the plastic is not good in adhesive property and so it is difficult to form an anti-fogging layer on the surface of the plastic.

According to the present embodiment, as shown in FIG. 1, since the transparent sheet 11 is formed by laminating the PET sheet 5 and the PP sheet 12, the film thickness of the transparent window can be made larger and so the heat-resistance property and the mechanical strength of the transparent window can be improved. In this case, since the PET sheet 5 having not-good transmission property is made thinner and the PP sheet 12 having good transmission property is made thicker, the decrease of an amount of transmission light can be prevented. Further, by making the transparent sheet 11 thicker, an error contained in the measured value of the concentration of the carbon dioxide due to the optical interference can be made smaller even if the thickness of the water layer formed on the anti-fogging layer 4 changes.

In the aforesaid embodiment, the thickness of the anti-fogging layer 4, the PET sheet 5 and the PP sheet 12 merely show an example and the thickness thereof are not limited to those values. Further, although in the aforesaid embodiment, the explanation has been made as to the case where the gas is the carbon dioxide, the present invention is effective in the case of measuring the concentration of gas such as anesthetic gas or other gas.

As described above, in the airway adapter for measuring the concentration of carbon dioxide according to the present invention, since the transparent film hermetically attached to the apertures portion is arranged in the laminated structure of the PET sheet and the PP sheet, the thickness of the film can be made larger without degrading the transmission property and both the heat-resistance property and the mechanical strength of the transparent window can be improved. Further, even if the thickness of the water layer formed on the fogging prevention film on the PET sheet changes, an amount of changes of the transmission light can be suppressed to a small value and an error contained in the measured value of the concentration of the carbon dioxide can be minimized.

What is claimed is:

1. An airway adapter for a non-dispersive infrared gas analyzer comprising:

a flow tube for passing gas therethrough;

aperture portions respectively formed by openings provided at opposite positions of a side wall of said flow tube and for passing an infrared ray therethrough, and a transparent film hermetically attached to said aperture portions, said transparent film including:
an anti-fogging layer disposed at an inner side of said flow tube;
a first film for forming an anti-fogging layer on the surface thereof; and
a second film layered on said first film and having transmittance characteristic for transmitting the infrared ray.

2. An airway adapter for a non-dispersive infrared gas analyzer according to claim 1, wherein said first film is made of a material selected from a group consisting of polyester, polycarbonate, vinyl chloride cellulose acetate and polyimide and said second film is made of one of a polypropylene and polyethylene.

3. An airway adapter for a non-dispersive infrared gas analyzer claimed in claim 1, wherein a thickness of said transparent member 50 $\mu$m or more.

4. An airway adapter for a non-dispersive infrared gas analyzer as claimed in claim 2, wherein a thickness of said transparent member is 50 $\mu$m or more.

* * * * *